(12) United States Patent
Ogawa et al.

(10) Patent No.: US 7,582,259 B2
(45) Date of Patent: Sep. 1, 2009

(54) BLOOD ANALYSIS DEVICE AND BLOOD ANALYSIS METHOD

(75) Inventors: Hiroki Ogawa, Yokohama (JP); Yasuhiro Horiike, Nishitokyo (JP)

(73) Assignee: Japan Science and Technology Agency, Saitama (JP)

( * ) Notice: Subject to any disclaimer, the term of this patent is extended or adjusted under 35 U.S.C. 154(b) by 643 days.

(21) Appl. No.: 10/546,447

(22) PCT Filed: Feb. 18, 2004

(86) PCT No.: PCT/JP2004/001802

§ 371 (c)(1), (2), (4) Date: Aug. 19, 2005

(87) PCT Pub. No.: WO2004/074846

PCT Pub. Date: Sep. 2, 2004

(65) Prior Publication Data

US 2006/0078873 A1    Apr. 13, 2006

(30) Foreign Application Priority Data

Feb. 19, 2003    (JP) ............................. 2003-040481

(51) Int. Cl.
*G01N 33/72*    (2006.01)
*C12Q 1/00*    (2006.01)
*C12M 1/34*    (2006.01)

(52) U.S. Cl. .......................... 422/72; 435/287.1; 435/4; 436/66

(58) Field of Classification Search ................... 422/72
See application file for complete search history.

(56) References Cited

U.S. PATENT DOCUMENTS

| 4,812,294 | A |   | 3/1989 | Combs |
| 6,123,119 | A | * | 9/2000 | Okumura ..................... 141/34 |
| 6,319,469 | B1 | * | 11/2001 | Mian et al. .................... 422/64 |

FOREIGN PATENT DOCUMENTS

| JP | 1-25058 A | 1/1989 |
| JP | 3-178641 A | 8/1991 |
| JP | 2000-42402 A | 2/2000 |
| JP | 2001-258867 A | 9/2001 |

OTHER PUBLICATIONS

Madoka Takai, "UJI Capillary Ketsueki Enshin Bunri Kino O Motsu Takomoku Sokutei Chip No Sakusei", 2002 Nen (Heisei 14 Nen) Shuki Dai 63 Kai Extended Abstracts; the Japan Society of Applied Physics, p. 1143, Separate vol. 3, p. 1143, Sep. 24, 2002.

* cited by examiner

*Primary Examiner*—Krishnan S Menon
*Assistant Examiner*—Rebecca Fritchman
(74) *Attorney, Agent, or Firm*—Sughrue Mion, PLLC

(57) ABSTRACT

A blood analysis device for centrifugally separating plasma in a channel, wherein conveyance of blood, plasma and calibration liquid is effected within the device without using a pump or the like. The calibrator solution is reliably discharged from a sensor portion so as to make high precision analysis possible. A sensor section is provided in a plasma separating section and disposed on the side associated with a first centrifugal pressing direction as seen from a blood reservoir and a calibrator solution reservoir, while a calibrator solution waste reservoir is disposed in a second centrifugal pressing direction as seen from the plasma separating section (sensor section). The calibrator solution is conveyed to the sensor section by centrifugal operation in the first centrifugal direction. After sensor calibration, the calibrator solution can be reliably discharged from the sensor section by effecting centrifuging in the second centrifugal direction. After the calibrator solution discharge, centrifuging is effected again in the first centrifugal direction, thereby conveying the blood in the blood reservoir to the sensor section and effecting separation of blood cells and plasma. In the case of providing a plurality of sensors, a blood introducing channel from the blood reservoir is branched downwardly of a sensor groove for communication, with the blood cells being fractionated in the branch section. The individual sensors can be isolated from each other by blood cell fraction, making higher precision analysis possible.

19 Claims, 10 Drawing Sheets

BLOOD ANALYSIS DEVICE AND BLOOD ANALYSIS METHOD

This is a National Stage application under 35 U.S.C. § 371 of PCT/JP2004/001802 filed on Feb. 18, 2004, which claims priority from Japanese patent application 2003-040481 filed on Feb. 19, 2003, all of which are incorporated herein by reference.

TECHNICAL FIELD

The present invention relates to a chip-shaped blood analysis device constituted by micro trench channels formed in an insulating substrate such as a quartz plate or a polymer resin plate. Particularly, the present invention relates to a channel structure for conveying liquids such as a calibrator solution for an analysis sensor and blood by a centrifugal force, when a small amount (several μL or less) of blood is introduced into trench channels on the chip, centrifugal separation is carried out to separate the blood into a blood cell and a plasma, and concentrations of various chemical material in the plasma are then measured.

BACKGROUND ART

In a conventional medical check-up or diagnosis of a disease state, several cc, a large amount of blood has heretofore been sampled from a patient, and the diagnosis has been carried out in accordance with measured values obtained by a large-scaled automatic blood analysis apparatus. Usually, this automatic analysis apparatus is large in size, and therefore is installed in a medical institution such as a hospital. Further, the apparatus is operated only by a person who has specialty qualification.

However, in recent years, there is increased a demand to develop a new device enable to grasp a health condition of a patient quickly and put such device to practical use. To the device, a fine working technique for use in preparing an extremely advanced semiconductor device is applied, analysis devices such as various sensors are arranged on a chip having a size of a several mm to several cm square at most, and a body fluid such as blood of a person being tested is applied to the device. By development of such inexpensive device, daily health cares of aged people could be managed at home in a coming aging society, and accordingly a health insurance benefit tracing a course to an increase would be compressed. Such device may realize quick diagnosis of presence of an infectious disease (hepatitis, acquired immune deficiency syndrome, etc.) of the person being tested and proper action thereafter in the field of the emergency medical care. Thus, various social effects could be expected, and therefore the device is in a technical field which has gotten a lot of attention. In this situation, in lieu of the conventional automatic analysis apparatus, there have been developed a small-sized simple blood analysis method and blood analysis device for personally performing blood analysis at home (e.g., Unexamined Japanese Patent Publication (KOKAI) JP 2001-258868 A; corresponding to WO 01/69242 A1 and US 2003/0114785 A1)).

FIG. 1 shows one example of a blood analysis device formed as a micro module described in JP 2001-258868 A. Reference numeral 101 denotes a lower substrate of the blood analysis device, and a micro trench channel (microcapillary) 102 is formed on the lower substrate by etching. An upper substrate (not shown) having a substantially equal size is laminated onto the lower substrate 101 to seal the trench channel 102 from the outside.

In the flow channel 102, blood sampling means 103, plasma separating means 104, analysis means 105, and moving means 106 are successively disposed from a most upstream portion toward a most downstream portion. A hollow blood collecting needle 103a is attached to the blood sampling means 103 which is provided on a most upstream end portion of the flow channel. A human body is stung with the needle 103a so that the needle constitutes an intake port of the blood into the substrate. The separating means 104 is formed by bending the flow channel 102 midway, and is constituted of, for example, a U-shaped microcapillary. After introducing the sampled blood into this U-shaped microcapillary, acceleration is applied to the substrate in a certain direction by a centrifuge, blood cell components are precipitated in a U-shaped lowermost portion, and a plasma is separated as a supernatant. The analysis means 105 includes sensors for measuring a pH value, and concentration of each of oxygen, carbon dioxide, sodium, potassium, calcium, glucose, lactic acid and the like in the blood.

The moving means 106 positioned in the most downstream portion of the flow channel moves the blood within the microcapillary by an electro-osmosis flow, and is constituted of electrodes 107, 108 and a flow channel portion 109 connecting both electrodes. A buffer solution with which the flow channel is filled previously is moved into the downstream side of the flow channel by the electro-osmosis flow generated by application of a voltage between the electrodes. And the blood is taken into the substrate from the blood sampling means 103 disposed at the front end of the channel 102 by a generated suction force. The plasma obtained by centrifugal separation is fed into the analysis means 105.

Reference numeral 110 denotes output means for taking information out of the analysis means, and comprises electrodes and the like, and 111 is control means for controlling the above-described sampling means, plasma separating means, analysis means, moving means, and output means, as needed.

The blood collected by the sampling means 103 is separated into plasma and blood cell components by the separating means 104, and the plasma is transferred into the analysis means 105. Then, the pH value in the plasma, and the respective concentrations of oxygen, carbon dioxide, sodium, potassium, calcium, glucose, lactic acid and the like in the plasma are measured. The movement of the blood between the respective means is performed by the moving means 106 having a pump function such as means using phenomena like electrophoresis and electro-osmosis. In FIG. 1, a downstream region of the flow channel 102 is branched into five, and each branch is provided with the analysis means 105 and moving means 106.

A glassy material such as quartz has been often used in the substrate of the blood analysis device, but, in recent years, a resin material has been regarded as more suitable for mass-producing the apparatuses at reduced costs, and used as a disposable material.

In the conventional blood analysis device shown in FIG. 1, when a blood sample is introduced into the device, the moving means like an electro-osmosis pump 106 is required. After centrifugally separating the introduced blood together with the substrate to obtain the plasma, the electro-osmosis pump 106 needs to be operated again in order to move this plasma to the analysis means 105. Especially when the analysis means is a sensor constituted based on an electrochemical principle, this sensor should be calibrated beforehand using a calibrator solution. Specifically, this sensor is immersed in the calibrator solution to calibrate the sensor before introducing the plasma into the sensor. After the calibration, the calibrator solution has to be discharged from the analysis means. The moving means like the pump is required also in transferring such calibrator solution.

Possible moving means for use is the electro-osmosis pump disposed in the same substrate as shown in FIG. 1, or a negative-pressure pump installed outside the substrate. By these moving means, the blood, the plasma, the calibrator solution and the like are fed under pressure, or sucked and moved. In this case, a suction force or the like of the movement means needs to be precisely controlled in order to move a desired liquid to a desired position in the blood analysis device. For this purpose, a position sensor for the liquid has to be newly installed in the inside or the outside of the blood analysis device, and there has been a problem that the device becomes expensive because such control mechanism or position sensor is added.

When the analysis means is the sensor constituted based on the electrochemical principle, the sensor is calibrated with a calibrator solution (standard solution) containing a component to be tested having a known concentration, and the calibrator solution has to be thereafter discharged from the analysis means. However, even when the calibrator solution is discharged, a slight amount of calibrator solution remains on the surface of the analysis means or flow channel means in accordance with wettability of the surface. As described above, in the blood analysis device which is the present object, sizes of means constituting devices like the flow channel means are reduced in such a manner as to analyze concentrations of various chemical substances in a small amount of several microliters of blood. In general, when a size of an object decreases, a ratio S/V of a surface area (S) to a volume (V) increases, and this means that the surface effect remarkably appears. Accordingly, even when the amount of the calibrator solution remaining on the surface of the flow channel or analysis means is small, the analysis device having a less amount of introduced plasma has a problem that the measured concentrations of the chemical substances are fluctuated. Therefore, after the calibration, the calibrator solution needs to be reliably discharged from the analysis means before the plasma is introduced into the analysis means.

The present invention has been developed in view of such situations, and a first object is to provide a blood analysis device which separates a plasma by a centrifugal operation in a flow channel and which can convey blood, plasma, and calibrator solution without using any pump or the like in the device and which more reliably discharges the calibrator solution from a sensor section so that high-precision analysis is possible.

Moreover, a second object of the present invention is to provide a blood analysis method in which blood, plasma, and calibrator solution can be conveyed only by a centrifugal operation in a blood analysis device in using the apparatus for separating the plasma in the flow channel by the centrifugal operation and which reliably discharges the calibrator solution from a sensor section so that high-precision analysis is possible.

DISCLOSURE OF THE INVENTION

According to the present invention, the first object is achieved by a blood analysis device which separates a plasma from a whole blood sample by centrifugation and analyzes a component to be analyzed in blood liquid components, comprising:

(a) a substrate comprising a sensor for analyzing the component to be analyzed in the blood liquid components;

(b) a plasma separating section provided in said substrate, and having a sensor groove for housing the sensor, the plasma being separated in the sensor groove when a centrifugal force is applied to the substrate in a first centrifugal direction;

(c) a blood introducing channel for communicating with said plasma separating section so that a blood sample is introduced into said plasma separating section when the centrifugal force is applied to the substrate in the first centrifugal direction;

(d) a calibrator solution introducing channel for communicating with said plasma separating section so that a calibrator solution is introduced into said plasma separating section, when the centrifugal force is applied to the substrate in the first centrifugal direction;

(e) a calibrator solution waste reservoir for communicating with said plasma separating section and allowing the calibrator solution in said plasma separating section to move therein, when the centrifugal force is applied to the substrate in a second centrifugal direction; and (f) a calibrator solution discharge channel which allows said plasma separating section to communicate with said calibrator solution waste reservoir, and discharges the calibrator solution in said plasma separating section to said calibrator solution waste reservoir, when the centrifugal force is applied to the substrate in the second direction.

That is, in the blood analysis device of the present invention, a centrifugal operation in two different directions is possible, and the calibrator solution in the calibrator solution introducing channel is conveyed to the plasma separating section (referred to also as a sensor section in the description) by the centrifugal operation in the first centrifugal direction. After sensor calibration, the substrate is centrifuged in the second centrifugal direction, and the calibrator solution can be reliably discharged from the plasma separating section (sensor section). After the calibrator solution discharge, centrifuging is effected again in the first centrifugal direction, thereby conveying the blood in the blood introducing channel to the plasma separating section (sensor section) and effecting separation of blood cells and plasma.

In a preferable embodiment, a blood reservoir for weighing is disposed midway in the blood introducing channel, or a calibrator solution reservoir for weighing is also disposed midway in the calibrator solution introducing channel.

The first and second centrifugal directions in which the centrifugal force is applied with respect to the substrate cross each other, preferably, substantially at right angles. For example, when the plasma separating section (sensor section) is provided on a lower side of a quadrangular substrate, the calibrator solution waste reservoir is disposed on a left side (or right side) crossing the lower side substantially at right angles. When the blood reservoir and the calibrator solution reservoir are provided, they are positioned in a center portion or an upper side of the substrate. Additionally, the first and second centrifugal directions do not necessarily cross each other substantially at right angles. When the blood sample is introduced into the blood reservoir and is centrifuged in the first centrifugal direction to separate the blood cells and the plasma, the calibrator solution waste reservoir may be positioned and a calibrator solution discharge channel may be disposed so that the calibrator solution should not flow back into the plasma separating section (sensor section).

The plasma separating section (sensor section) may be provided with a plurality of sensor grooves, and a plurality of sensors for analyzing different components to be analyzed may be housed in the respective sensor grooves. In this case, the blood introducing channel is branched to communicate with each of the plurality of sensor grooves in a first centrifugal force pressurizing direction (substrate lower side). In the blood introducing channel, preferably, a portion positioned in the first centrifugal force pressurizing direction (substrate lower side) from the sensor section preferably has a capacity for containing a blood cell fraction of the blood in a case where the substrate is centrifuged in the first centrifugal direction. The plasma contacting with one of the sensors is isolated from the plasma contacting with the other sensor by blood cell fraction. Therefore, even when a hydrogen ion concentration locally fluctuates by an electrochemical reaction performed by a sensor operation, the other adjacent sensor is not influenced.

When a blood collecting needle is attachable to a blood intake port of the blood introducing channel in the substrate, whole blood collected via the blood collecting needle can be introduced directly into the blood reservoir. When the blood reservoir and the blood introducing channel are subjected to a hydrophilic treatment beforehand, the blood sample can be smoothly introduced.

A second object of the present invention can be achieved by a blood analysis method comprising the steps of:

(a) providing a blood analysis device comprising a substrate provided with a sensor; a plasma separating section disposed in the substrate, having a sensor groove which houses the sensor, and separating a plasma in the sensor groove; a blood introducing channel which introduces a blood sample into the plasma separating section; a calibrator solution introducing channel which introduces a calibrator solution into the plasma separating section; a calibrator solution waste reservoir; and a calibrator solution discharge channel which connects the plasma separating section to the calibrator solution waste reservoir, and discharges the calibrator solution in the plasma separating section to the calibrator solution waste reservoir;

(b) supplying the calibrator solution to said calibrator solution introducing channel;

(c) applying a centrifugal force to the substrate in a first centrifugal direction in such a manner that said plasma separating section is disposed in a centrifugal force pressurizing direction, so as to introduce the calibrator solution in the calibrator solution introducing channel into said sensor groove of the plasma separating section;

(d) calibrating said sensor;

(e) rotating said substrate with positioning the substrate in a second centrifugal direction to centrifuge the substrate in such a manner that said calibrator solution reservoir is disposed in the centrifugal force pressurizing direction, and discharging the calibrator solution in the sensor groove to the calibrator solution waste reservoir;

(f) introducing a blood sample into said blood introducing channel;

(g) applying the centrifugal force to the substrate in the first centrifugal direction in such a manner as to dispose the plasma separating section in the centrifugal force pressurizing direction, whereby the blood sample is transferred to the plasma separating section with allowing the plasma separating section to separate blood cells from the plasma, so as to introduce the separated plasma into the sensor groove; and (h) analyzing a liquid component of the plasma in the sensor groove by the sensor.

BEST MODE FOR CARRYING OUT THE INVENTION

First Embodiment

Figure 1:
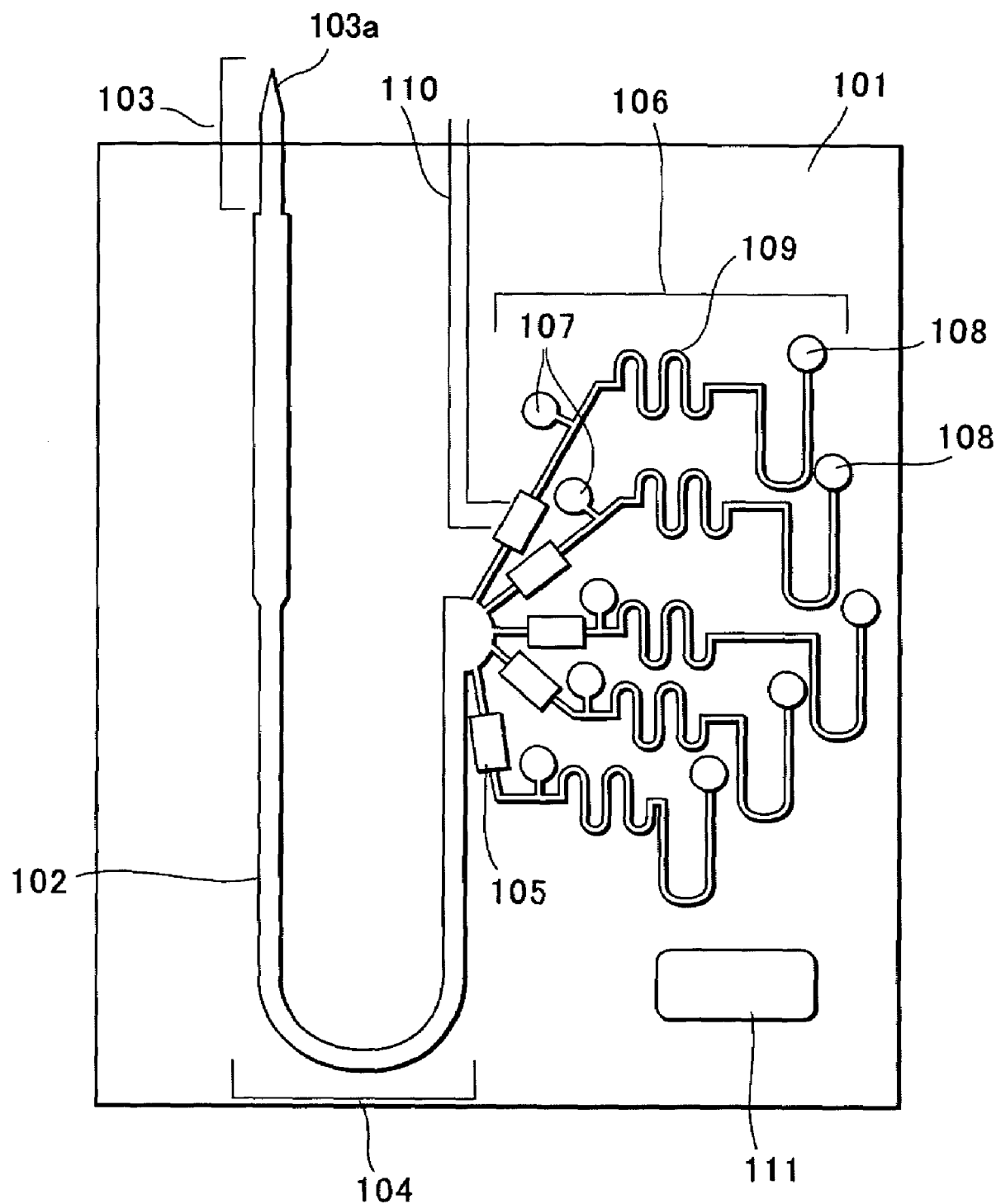
FIG. 1 is a schematic diagram of a conventional chip-shaped blood analysis device.
Figure 2:
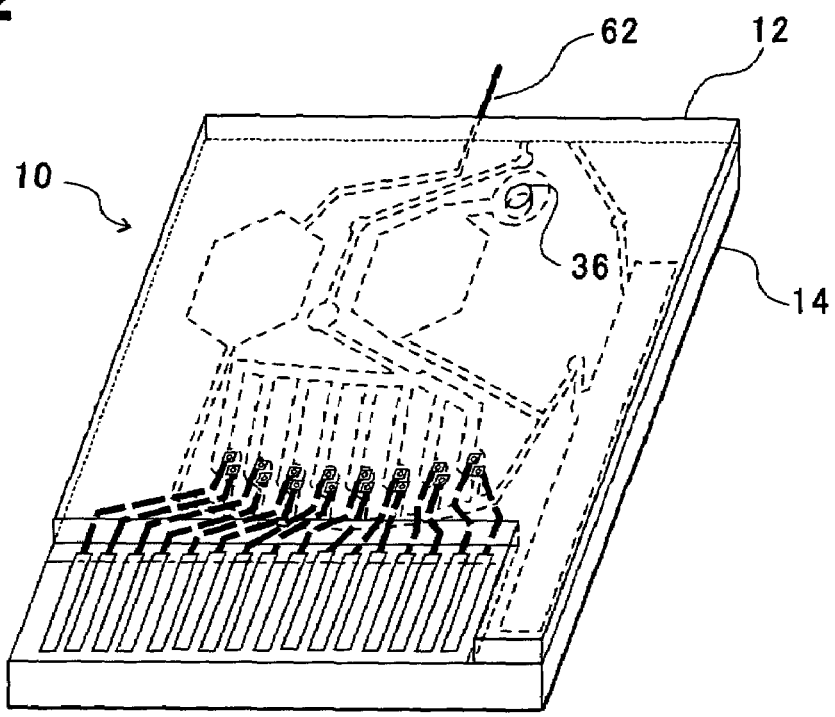
FIG. 2 is a whole perspective view of a chip-shaped blood analysis device according to a first embodiment of the present invention.
Figure 3:
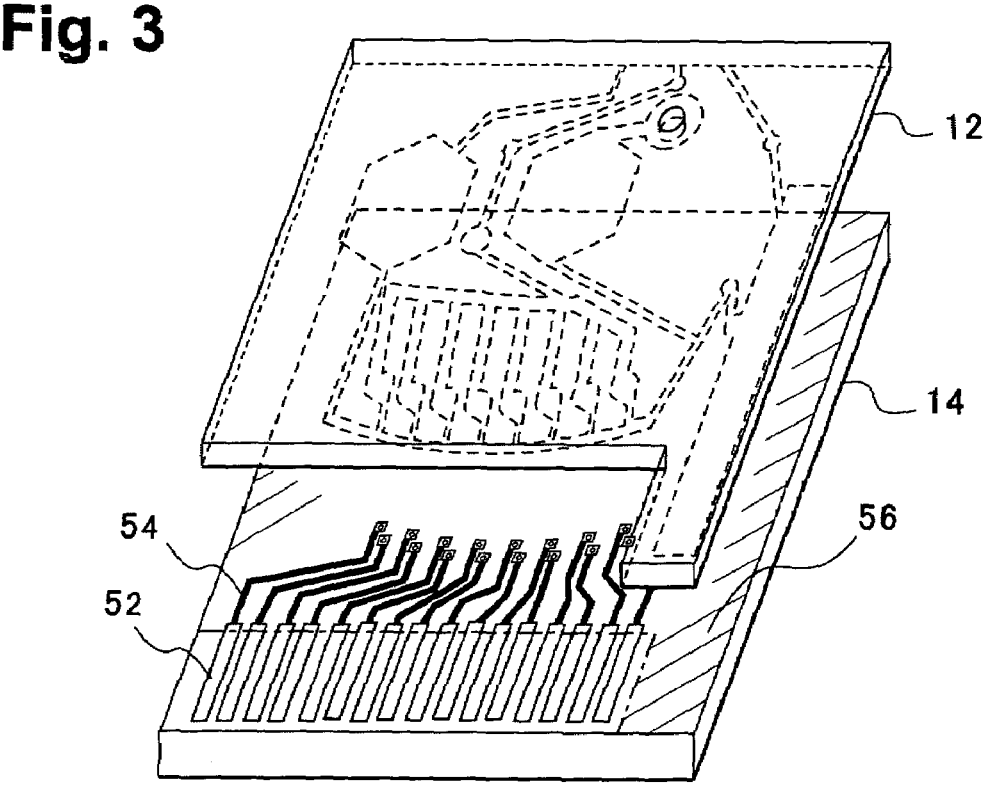
FIG. 3 is an exploded perspective view of the blood analysis device of FIG. 2.
Figure 4:
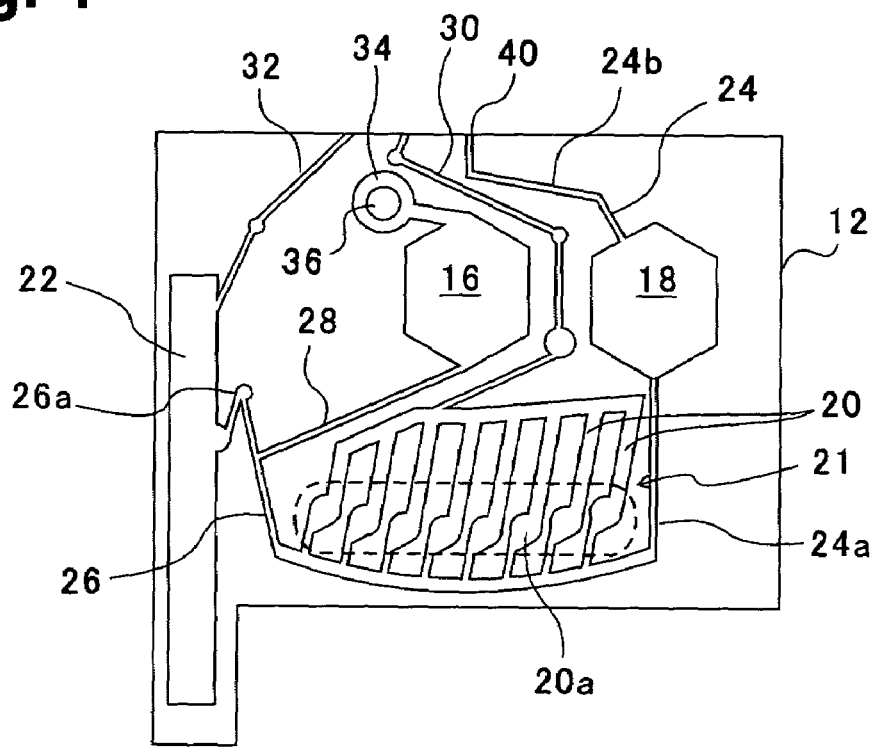
FIG. 4 is a bottom plan view of an upper substrate of the blood analysis device of FIG. 2.
Figure 5:
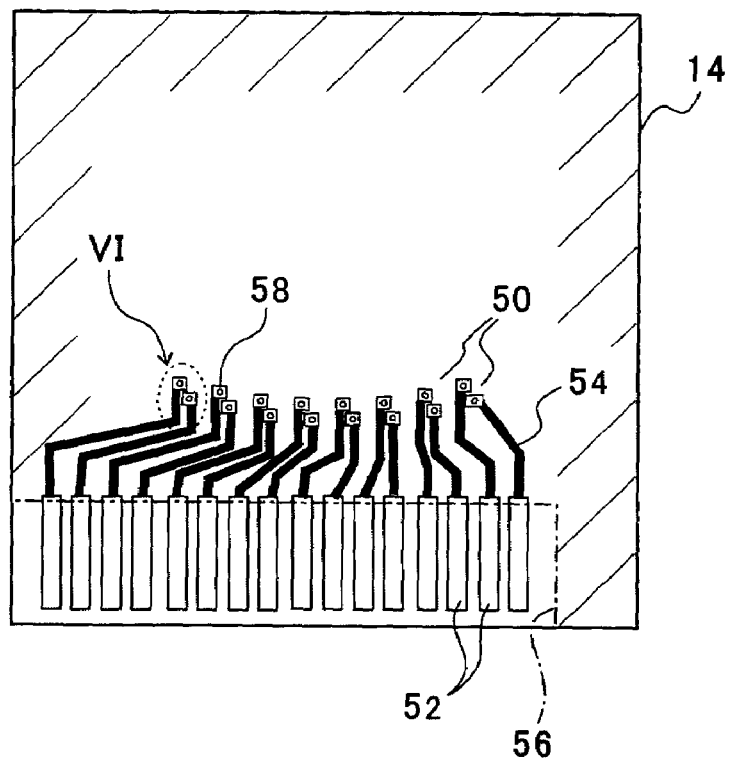
FIG. 5 is a plan view of a lower substrate of the blood analysis device of FIG. 2.

FIG. 2 is a perspective view of a blood analysis device according to a first embodiment of the present invention, FIG. 3 is an exploded perspective view, FIG. 4 is a bottom plan view of an upper substrate, and FIG. 5 is a plan view of a lower substrate. In these figures, reference numeral 10 denotes a blood analysis device, and an upper substrate 12 is overlaid on a lower substrate 14. The upper and lower substrates 12, 14 are, for example, made of resins such as polyethylene terephthalate (PET) and polycarbonate (PC).

In a bottom surface of the upper substrate 12, as shown in FIG. 4, a calibrator solution reservoir 16 and a blood reservoir 18 are provided slightly nearer an upper side of the figure, a plasma separating section (sensor section) 21 is disposed beneath, and a calibrator solution waste reservoir 22 is laterally disposed. The plasma separating section (sensor section) 21 is provided with a plurality of sensor grooves 20, and each sensor groove 20 has an enlarged diameter portion 20a which corresponds to an electrode on the lower substrate 14 described later. Reference numeral 24 denotes a flow channel which introduces a blood sample into the sensor section 21, and the blood reservoir 18 is disposed midway in the flow channel. A lower blood introducing channel 24a which connects the blood reservoir 18 to the sensor grooves 20 is branched downwardly of the sensor grooves 20, and is connected to the lower portion of each sensor groove 20. The branched portion of the lower blood introducing channel 24a also communicates with a calibrator solution discharge channel 26. Accordingly, the sensor grooves 20 communicate with the calibrator solution waste reservoir 22. Reference numeral 26a denotes a backflow preventive weir for preventing a backflow from the calibrator solution waste reservoir 22 to the sensor section 21. Reference numeral 28 denotes a calibrator solution introducing channel, and introduces a calibrator solution in the calibrator solution reservoir 16, which is disposed midway of the channel, into each sensor groove 20. Reference numerals 30, 32 denote air vent trench channels. A recess well 34 is disposed upwardly of the calibrator solution reservoir 16 as seen in the figure and communicate with this reservoir. The recess well 34 has a through hole 36 in the center thereof, which introduces the calibrator solution from the outside of the substrate. It is to be noted that 24b denotes an upper blood introducing channel for introducing the blood into the blood reservoir 18, and a blood collecting needle is attachable to an inlet port 40 of the channel 24b. These recessed structures are formed as minute trench channel structures in the resin substrate by injection or molding using a mold. Each of the trench channels 20, 24 (24a, 24b), 26, 28, 30, 32 has a width of several hundreds of μm, and a depth of a recess other than the through hole 36 is all 100 μm including the trench flow channel. A capacity of the blood reservoir 18 corresponds to a sufficient blood amount of 1 μL required for blood analysis. The calibrator solution reservoir 16 also has a substantially equal capacity of 1 μL.

On the lower substrate 14, as shown in FIG. 5, there are disposed a plurality of sensor electrodes 50, output pads 52 from which sensor output signals are picked up, and wires 54 which interconnect them. Each of these portions can be formed into a thickness of 10 to 20 μm in the resin substrate, for example, by use of a screen printing process.

A photopolymerization sensitive film 56 having a thickness of about 50 μm is laminated on the lower substrate 14 in such a manner as to expose a part of the pads 52 (FIG. 5, slant line portion). In this case, the film 56 is laminated while applying an appropriate pressure or heat to the film. Accordingly, irregularities on the resin substrate 14 due to the thicknesses of the sensor electrodes 50 and the wires 54 are eliminated to smoothen the surface. Thereafter, a part of the film on each sensor electrode 50 is subjected to ultraviolet exposure and development, thereby an aperture 58 is formed so as to expose a part of the sensor electrodes 50.

It is to be noted that these electrodes, wires, and pads may be formed by use of another metal film forming process such as sputtering or plating.

The upper substrate 12 of FIG. 4 is reversed upside down and overlaid on the thus formed lower substrate 14 to prepare the substrate 10 (FIGS. 2, 3). The recessed structure in the bottom surface of the upper substrate 12 is sealed with the lower substrate 14, the aperture 58 in the lower substrate are positioned beneath the enlarged diameter portions 20a of the sensor grooves 20, and a pair of sensor electrodes 50 are exposed in the respective sensor grooves 20 to constitute the respective sensors. The sensor section 21 is constituted by the plurality of sensor electrodes 50 of the lower substrate and the plurality of sensor grooves 20 of the upper substrate. In the case that one of the sensor electrodes 50 is coated with an ion sensitive membrane or an enzyme immobilized membrane, and the other sensor electrode is constituted as a reference electrode, a pair of these sensor electrodes 50 constitutes a sensor for analyzing a certain type of chemical substance.

Figure 6:
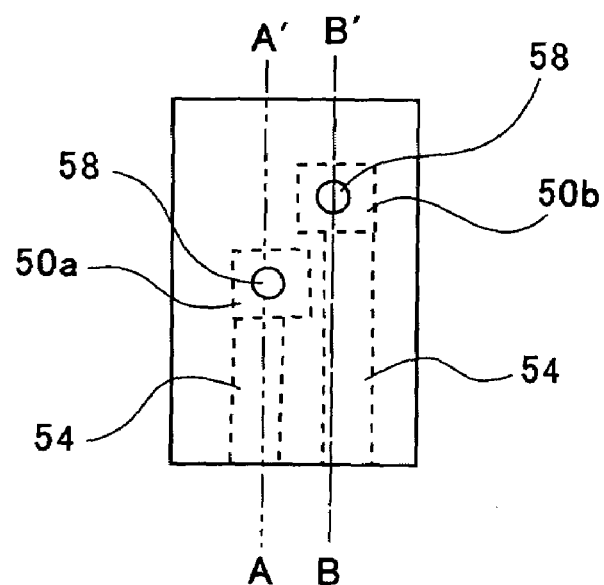
FIG. 6 is an enlarged view of a region VI of FIG. 5.
Figure 7A:
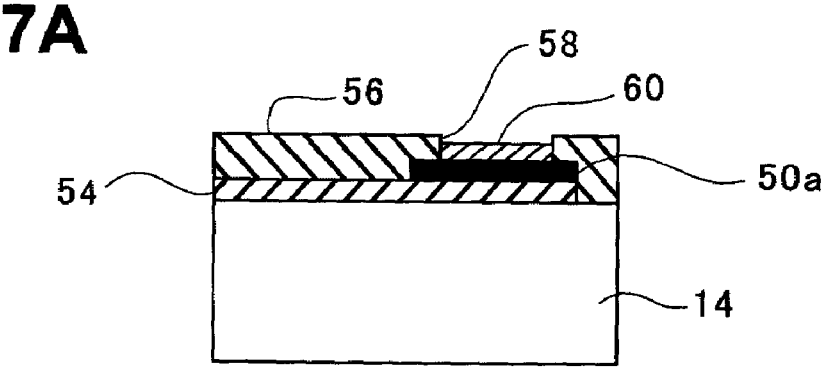
FIGS. 7A, B are sectional views along lines A-A' and B-B' of FIG. 6, respectively.
Figure 7B:
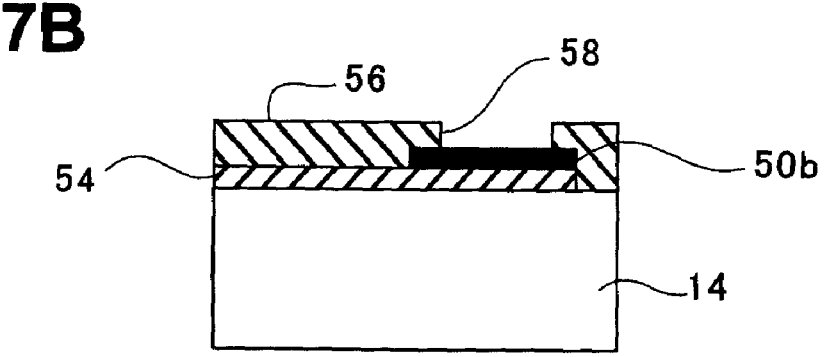

A structure of the pair of sensor electrodes will be described with reference to FIGS. 6, 7. FIG. 6 is an enlarged view of an upper surface of a dotted line part VI of FIG. 5, and FIGS. 7A, B show partially sectional views along lines A-A' and B-B' of FIG. 6.

In general, there are a potential measuring type of potentiometry process and a current measuring type of amperometry process in electrochemical sensing by use of the electrodes. In the potentiometry, each electrode is coated beforehand with a membrane (ion sensitive membrane) sensitive to ions of hydrogen, sodium, potassium, calcium, ammonia and the like in a solution, and a potential difference between the electrode in the solution containing the ion as a measurement object and the reference electrode is proportional to a logarithm of an ion concentration in the solution (Nernst response). Accordingly, the concentration of the ion which is the object is measured.

In the potentiometry, in a pair of sensor electrodes 50, one electrode 50a is coated with the membrane which is sensitive to a specific ion, and the reference electrode (Ag/AgCl electrode) is used in the other electrode 50b. More specifically, as shown in FIG. 6, the electrode 50a exposed in the aperture 58 is coated with an ion sensitive membrane 60. An Example of the electrode 50a used herein may be constituted by drying carbon paste. Moreover, the other electrode 50b which is used as the reference electrode may be an Ag/AgCl electrode formed on the wire 54 by a screen printing process.

By use of the certain ion sensitive membrane, the potentiometry process can be used not only in analysis of a hydrogen ion concentration (pH) and the concentration of the sodium, potassium, or calcium ion in blood plasma, but also in analysis of concentrations of components other than the ions in a plasma. Such components include blood urea nitrogen (BUN), lactic acid, and creatinine. For example, when urea nitrogen is analyzed, an ammonia ion sensitive membrane is used in the ion sensitive membrane 60, and urease is immobilized in the membrane beforehand. As to blood urea nitrogen in plasma, the following reaction proceeds by a function of urease:

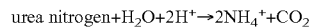

urea nitrogen+$H_2O$+$2H^+$→$2NH_4^+$+$CO_2$

When a concentration of generated ammonia ions is measured, the urea nitrogen concentration can be obtained. It is to be noted that hydrogen ions ($H^+$) are consumed in the reaction and the concentration thereof decreases. Therefore, the urea nitrogen concentration can be measured even by use of the hydrogen ion sensitive membrane. Similarly, the creatinine concentration in the plasma can be analyzed by the potentiometry process.

On the other hand, the amperometry process is a method in which a voltage is applied between a pair of electrodes, and the concentration of an object chemical substance in the blood or plasma is analyzed from a value of a current flowing at this time. In this case, instead of the ion sensitive membrane 60 shown in FIG. 7, an enzyme-immobilized membrane is used as an anode, and the exposed sensor electrode 50b is used as a cathode. A principle of sensing by this electrode pair will be briefly described in the case that an object to be analyzed is glucose.

As to glucose (β-D-glucose) in a liquid (blood or plasma in this case), the following reaction proceeds by a function of enzyme (glucose oxidase in this case) immobilized on an anodic electrode.

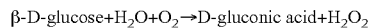

$$\beta\text{-D-glucose} + H_2O + O_2 \rightarrow \text{D-gluconic acid} + H_2O_2$$

An amount of generated hydrogen peroxide ($H_2O_2$) is proportional to a glucose concentration. The voltage is applied between the electrodes to electrolyze hydrogen peroxide as ($H_2O_2 \rightarrow 2H^+ + O_2 + 2e^-$) on the anode. At this time, $e^-$ (electron) is generated. This means that a current flows via the electrode. Namely, this current amount is substantially proportional to the glucose concentration. Therefore, the glucose concentration can be known by measuring the current amount.

As to an electrochemical sensor by the above-described potentiometry or amperometry process, an analysis result is influenced by environmental conditions (temperature, etc.) at an analysis time, or fluctuations of thicknesses of certain membranes constituting the sensor. Therefore, prior to the analysis of a sample to be analyzed, the calibrator solution containing a chemical substance to be analyzed having a known concentration is fed into the sensor, an output of the sensor is checked, and the sensor is calibrated. This is indispensable for obtaining the analysis result having a high reliability.

In the present embodiment, eight types of electrochemical sensors by such potentiometry and amperometry processes were formed with respect to eight pairs of electrodes as shown in FIG. 5. In details, there are the hydrogen ions, sodium ions, potassium ions, calcium ions, glucose, urea nitrogen, creatinine, and lactic acid. After coating the electrode 50a with the ion sensitive membrane or an oxygen-containing membrane constituting the sensor, as shown in FIG. 2, the upper and lower substrates 12, 14 are laminated. And then, a painless needle 62 constituted by sharply polishing a tip of a tube having an outer diameter of 100 microns and an inner diameter of 50 microns is attached to a tip of a chip.

Next, a method of using this blood analysis device will be described with reference to FIGS. 8 to 13. It is to be noted that in these figures, the sensor electrodes 50 and the wires 54 are partially omitted from the drawing. First, the sensor is calibrated before the blood analysis.

Calibration of Sensor

Figure 8:
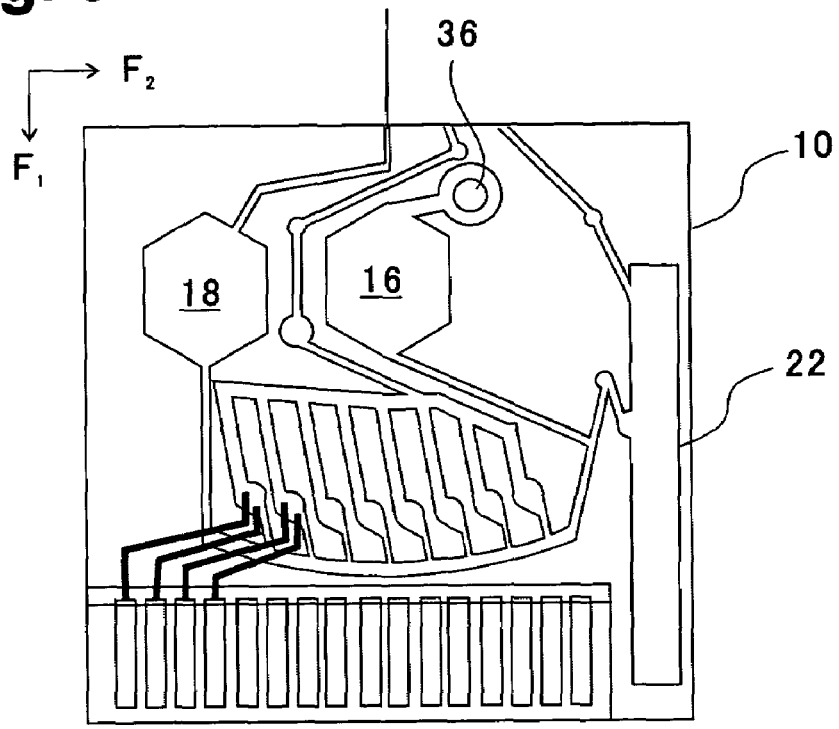
FIG. 8 is a diagram showing a state of the chip-shaped blood analysis device of the first embodiment before used.
Figure 9:
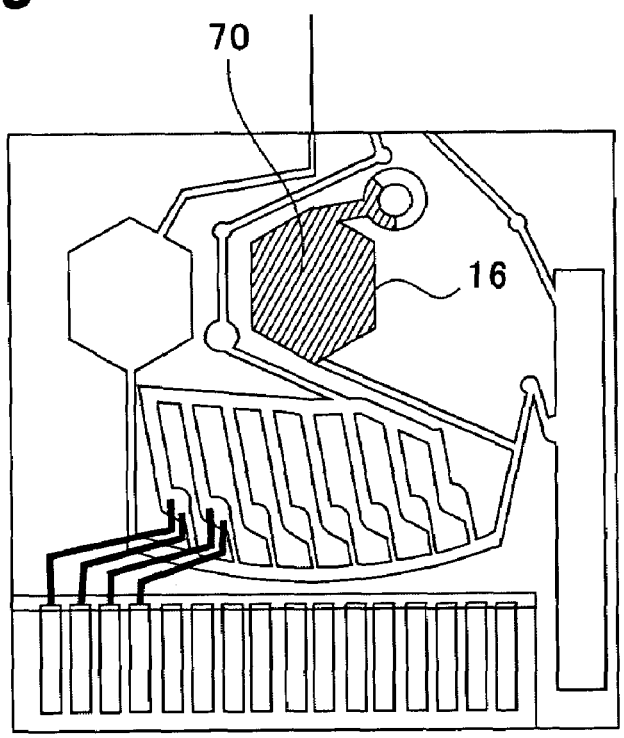
FIG. 9 is a diagram showing that a calibrator solution is introduced into the chip-shaped blood analysis device of the first embodiment.
Figure 10:
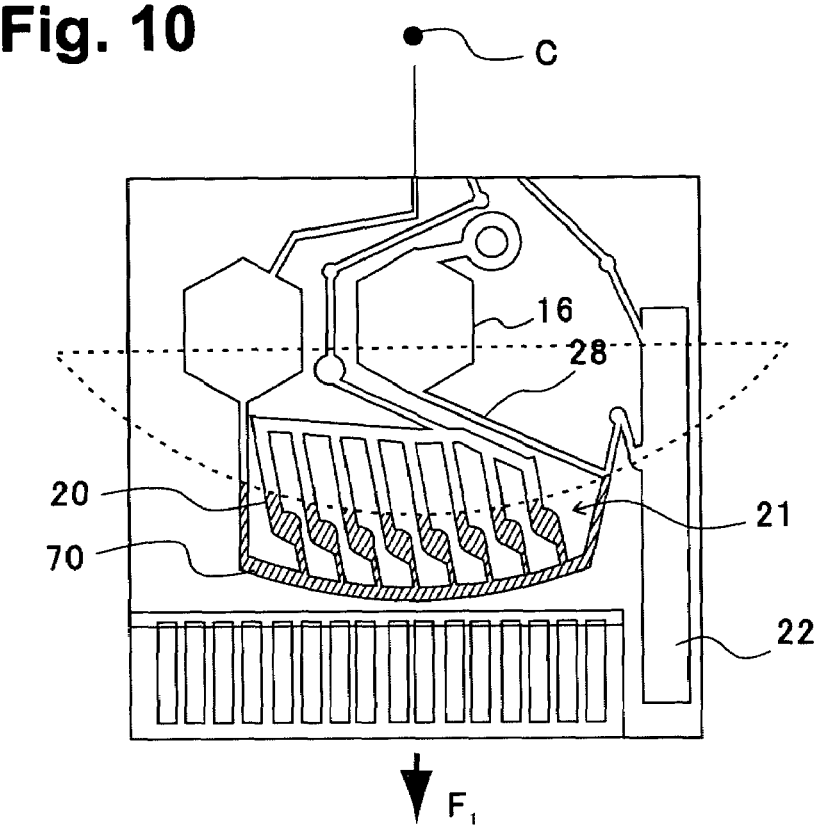
FIG. 10 is a diagram showing that the calibrator solution is transferred to a sensor groove by centrifugation.

A calibrator solution 70 is introduced from the through hole 36 in the upper surface of the blood analysis device 10 of FIG. 8 until the calibrator solution reservoir 16 is filled as shown in FIG. 9. When this calibrator solution reservoir 16 is filled, the calibrator solution 70 substantially having a capacity of 1 μL is weighed. This calibrator solution may be introduced immediately before performing the blood analysis, or may be introduced beforehand in the calibrator solution reservoir in the blood analysis device. After introducing the calibrator solution into the blood analysis device 10, the device is attached to the a centrifugal separation apparatus shown in FIG. 14 to perform a centrifugal operation. At this time, the blood analysis device 10 is set in such a manner that the plasma separating section (sensor section) 21 in the device is positioned in a centrifugal direction, that is, a pressurizing direction of a centrifugal force $F_1$. By this centrifugal operation, the calibrator solution 70 passes through the calibrator solution introducing channel 28, transfers to each sensor groove 20 of the sensor section, and covers the sensor electrode (FIG. 10). In this state, each sensor is calibrated. It is to be noted that symbol C in FIG. 10 denotes a centrifugal center axis, and symbol $F_1$ denotes the centrifugal pressurizing direction.

Discharging of Calibrator Solution

Figure 11:
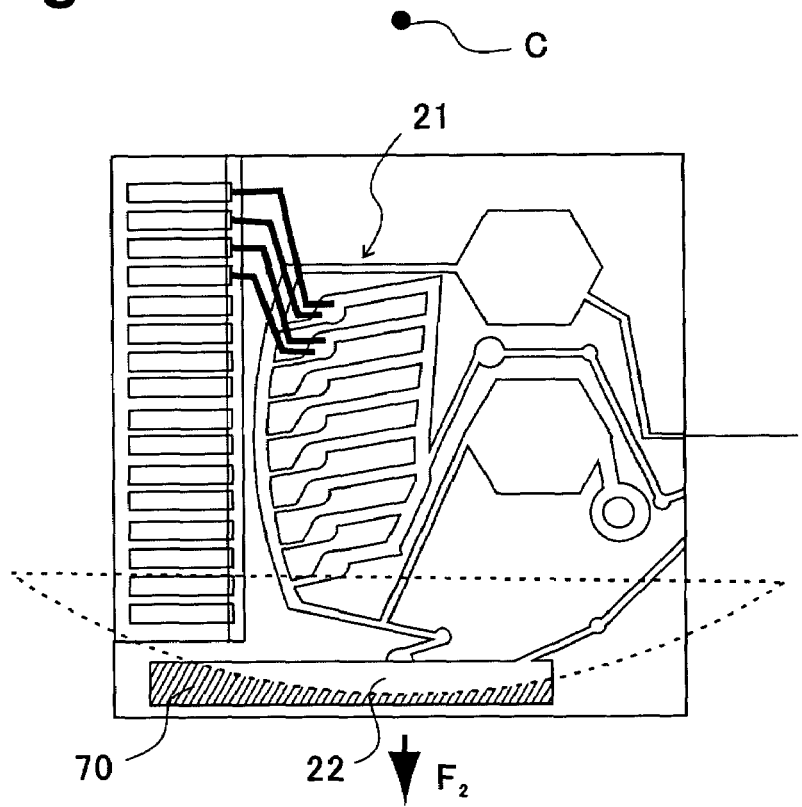
FIG. 11 is a diagram showing that the calibrator solution after calibration is discharged to a waste reservoir by the centrifugation.

After calibrating the sensor, the calibrator solution in the sensor section 21 is discharged. As shown in FIG. 11, the analysis device 10 is rotated in a clockwise direction by 90 degrees, and is attached to the centrifugal separation apparatus of FIG. 14 in such a manner that the calibrator solution waste reservoir 22 is positioned on a lower side of the figure, that is, in a second centrifugal direction $F_2$ to perform the centrifugal operation. With such operation, the calibrator solution 70 in the sensor grooves 20 moves to the calibrator solution waste reservoir 22, and the discharging of the calibrator solution is completed. When a sufficient centrifugal force is applied, the calibrator solution can be completely discharged. Accordingly, an error in an analyzed value by a remaining calibrator solution is not generated.

Introduction of Blood

Figure 12:
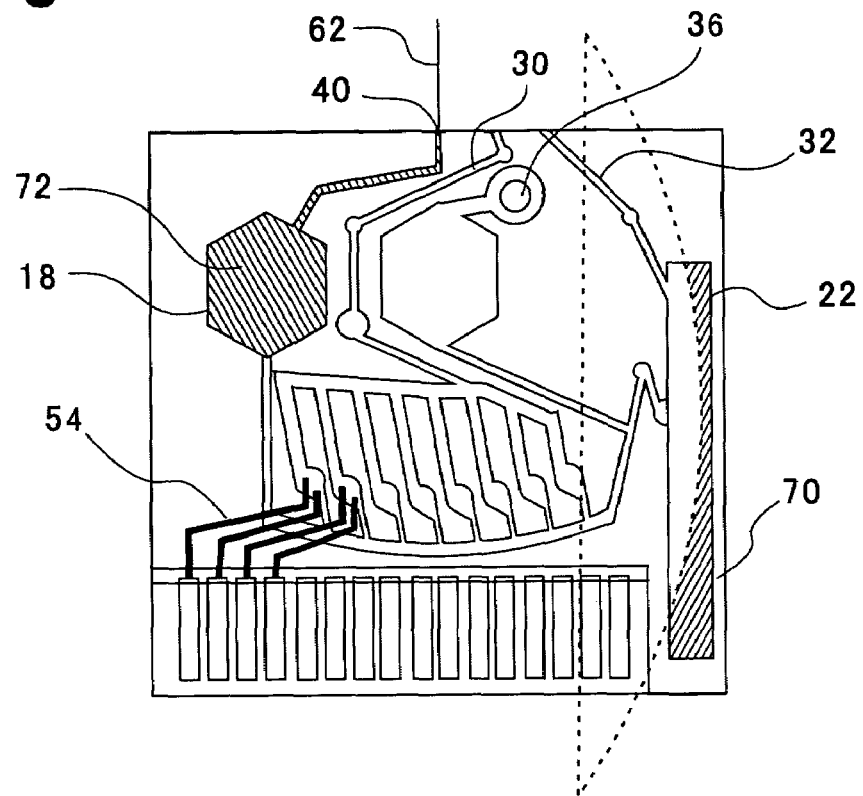
FIG. 12 is a diagram showing that blood is introduced into a blood reservoir in the chip-shaped blood analysis device.

Next, as shown in FIG. 12, the painless blood collecting needle 62 is attached to the blood inlet port 40 of the substrate 10, and human skin is stung with this needle to introduce whole blood 72 into the blood reservoir 18. When the blood reservoir 18 is filled, a sufficient blood amount of 1 μL required in the analysis can be weighed. When this blood is introduced, the skin is pierced with the painless needle 62 while closing the air vent channels 30, 32, and the blood is sucked through the through hole 36 by the negative-pressure pump to introduce the blood. The channel 32 which communicates with the calibrator solution waste reservoir 22 is interrupted, and therefore the calibrator solution 70 in the waste reservoir 22 does not flow backwards at the time of the blood introduction.

Blood Conveyance and Separation of Blood Cell/Plasma

Figure 13:
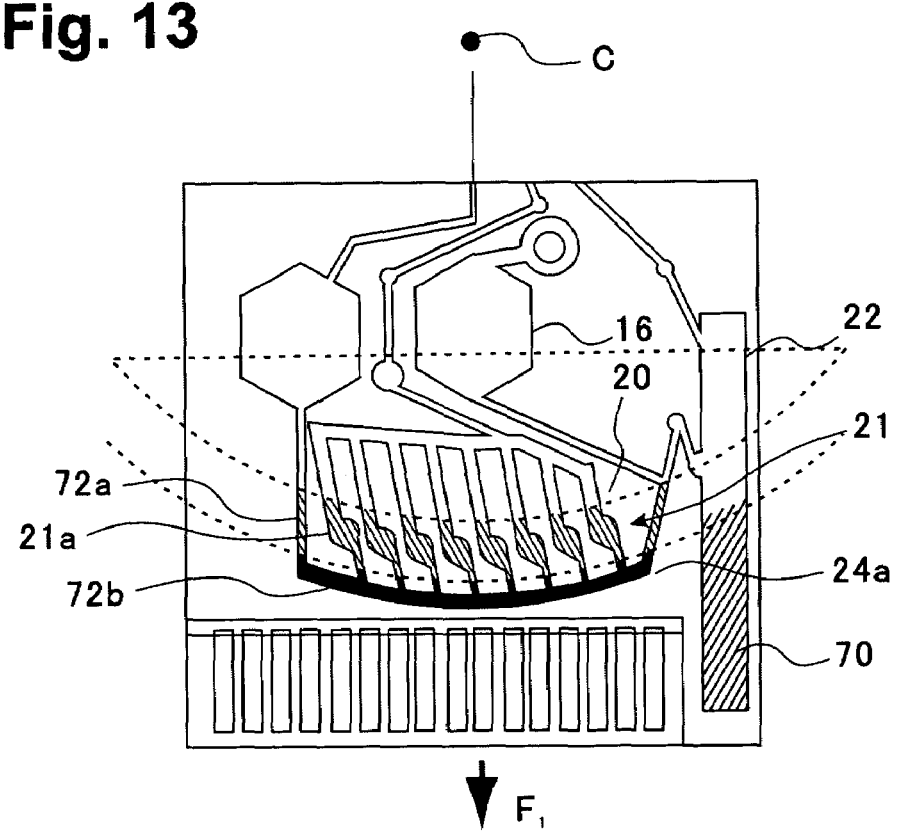
FIG. 13 is a diagram showing that centrifuging is effected, thereby conveying the blood to the sensor grooves and separating blood cells and plasma.

Thereafter, the blood is transferred to the plasma separating section (sensor section), and is separated into blood cells and plasma. As shown in FIG. 13, the blood analysis device is attached to the centrifugal separation apparatus of FIG. 14 in such a manner that the sensor section 21 is positioned on the lower side of the figure, that is, in the first centrifugal direction (centrifugal force pressurizing direction) $F_1$ to perform the centrifugal operation. By the centrifugation, the blood 72 moves to the plasma separating section (sensor section) 21, and blood cells and plasma components are separated by the centrifugal force. A blood cell fraction 72b is fractionated in the branched portion of the blood introducing channel 24a, and plasma 72a is fractionated in the sensor grooves 20 disposed above. As shown in FIG. 13, the channel is designed in such a manner that the plasma 72a is positioned in the enlarged diameter portions 21a of the sensor grooves which house the sensor electrodes. In general, a blood cell component ratio to a total volume of the blood is 34 to 48%. Therefore, when the flow channel around the sensor electrode is designed in consideration of this ratio, the separated plasma components can automatically come on the sensor electrodes after the centrifugal separation. Accordingly, unlike the conventional method, the plasma component does not have to be guided into the sensor electrode via a pump or the like after the centrifugal separation.

Finally, the blood analysis device (substrate) 10 is detached from the centrifugal separation apparatus, and a component to be analyzed in the plasma housed in each sensor groove 20 is analyzed by each sensor electrode 50. At the analysis, the respective sensor grooves 20 are interrupted from one another by the blood cell fraction 72b. Therefore, the respective pairs of sensor electrodes 50a, 50b are insulated from one another, and are not easily influenced by electrochemical reactions in the other sensors. For example, when the urea nitrogen concentration is analyzed as described above, the hydrogen ions are consumed by the reaction of urease, and the hydrogen ion concentration locally decreases. When the glucose concentration is analyzed, the hydrogen ions are generated by electrolysis of hydrogen peroxide, and the hydrogen ion concentration therefore increases. When the sensor electrode for glucose measurement is disposed adjacent to the hydrogen ion concentration sensor, it is easily predicted that the analysis result is adversely affected by the fluctuation of the hydrogen ion concentration in each sensor. Especially, this phenomenon becomes remarkable in a case where a channel dimension is small, and a blood capacity is small as in the chip-shaped analysis device. In the blood analysis device of the present invention, since the respective sensor electrodes are insulated from one another by the blood cell components, the blood cell components can serve as barriers to inhibit an interaction between the sensors.

Second Embodiment

Figure 16:
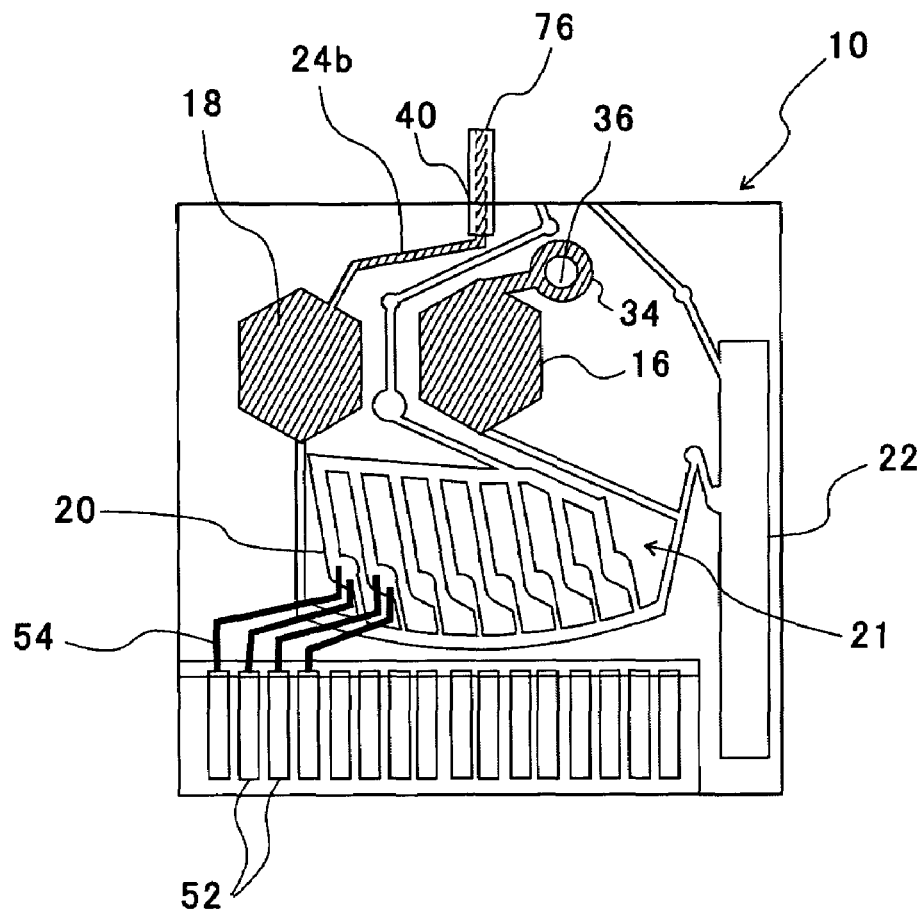
FIG. 16 is a schematic plan view of a blood analysis device according to a second embodiment in which a hydrophilic treatment is performed.

FIG. 16 shows a blood analysis device according to a second embodiment of the present invention. This analysis device 10 is different from the first embodiment in that, as shown by slant lines in the figure, inner walls of a blood reservoir 18, an upstream blood introducing channel 24b, and an inlet port 40, and channel inner walls of a through hole 36 to a calibrator solution reservoir 16 are subjected to a hydrophilic treatment. Instead of a blood collecting needle, a blood collecting cylinder 76 is attached to the blood intake port 40. Another structure is the same as that of the first embodiment.

Figure 17:
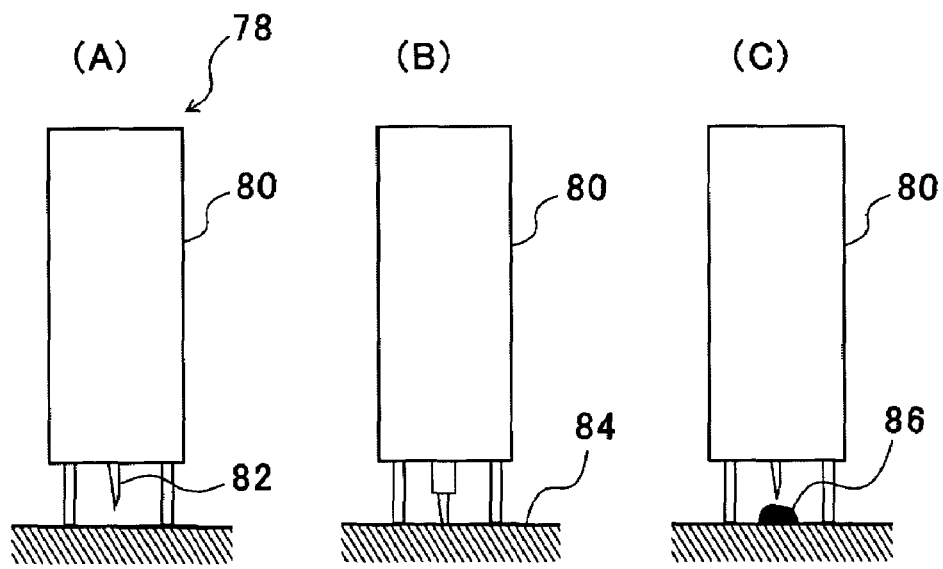
FIG. 17 is an explanatory view of a capillary blood sampling device for use in the second embodiment.

In the blood analysis device of the first embodiment, blood and calibrator solution can be conveyed utilizing a centrifugal force, but suction using a pump is required for collecting the blood from a person being tested. The second embodiment uses a capillary blood sampling device 76 for use in a blood sugar (glucose) value inspection performed by each person at home at present. About several μL of blood exuded on skin can be introduced into the blood analysis device via the hollow blood collecting cylinder 76. In a capillary blood sampling device 78, as shown in FIG. 17, a main body 80 is provided with a piercing needle 82. A skin surface 84 is slightly scratched by the action of a spring installed in the main body (part (B) of the figure), and about several μL of capillary blood 86 is exuded from the scratch (part (C) of the figure).

The blood collecting cylinder 76 is, for example, a hollow cylinder having an outer diameter of 300 μm and an inner diameter of 150 μm and made of a polycarbonate resin, and an inner wall of the cylinder is formed to be hydrophilic by an ozone treatment. In the present embodiment, the inner wall of the channel 24b in the region from the intake port 40 to the blood reservoir 18 is subjected to a hydrophilic treatment in order to smoothly introduce the blood from the blood collecting cylinder 76 to the blood reservoir 18. Similarly, the inner wall of the through hole 36 to the calibrator solution reservoir 16 is also subjected to the hydrophilic treatment (slant line of FIG. 16). By this hydrophilic treatment, the blood can be easily introduced into the blood reservoir by a capillary function without using any suction pump. When the through hole 36 is only spotted with a necessary amount of calibrator solution, the solution can also be introduced into the calibrator solution reservoir. The solution does not shift to another portion until the subsequent centrifugal operation is performed.

Figure 18:
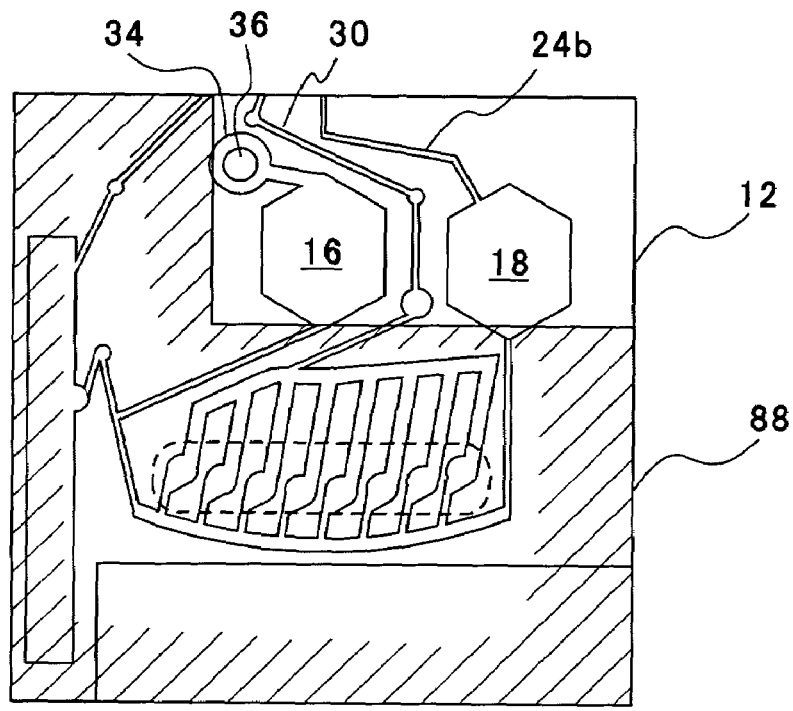
FIG. 18 is an explanatory view of a method for effecting hydrophilic treatment to a part of an upper substrate bottom surface in the second embodiment.

The hydrophilic treatment can be performed, for example, as follows. As shown in FIG. 18, a mask plate 88 made of aluminum is laid on the upper substrate 12 made of a PET resin in which the same channel structure as that of FIG. 4 is formed. This mask plate 88 covers a region (slant line portion of FIG. 18) other than the calibrator solution reservoir 16, the blood reservoir 18, the blood introducing channel 24a, and the through hole 36 for introducing the calibrator solution. In this state, the upper substrate 12 is exposed to an oxygen plasma. As to the oxygen plasma, for example, in an oxygen pressure of 133 Pa, a microwave of 2.45 GHz is guided to a plasma cavity to generate the oxygen plasma. An incident power is 100 W, and a treatment time is 30 seconds. The PET resin surface of a portion which is not covered with the mask 88 is oxidized by oxygen atoms, when exposed to the oxygen plasma, and hydrophilicity increases. A water droplet contact angle of the surface of the resin substrate can be reduced from about 70 degrees before the treatment to about 15 degrees after the treatment, and it can be confirmed that the hydrophilicity increases by this oxygen plasma treatment.

Figure 19:
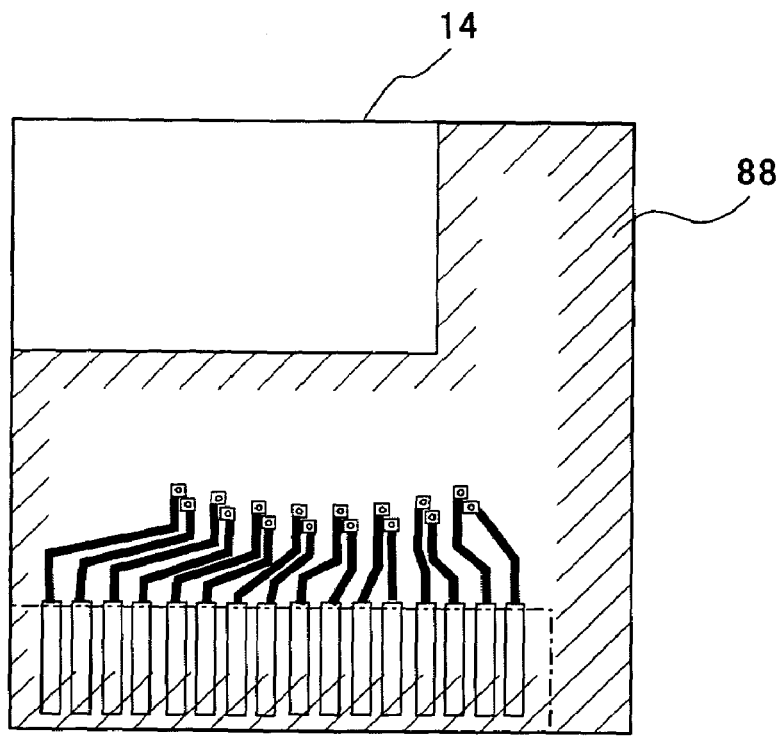
FIG. 19 is an explanatory view of a method for effecting hydrophilic treatment to a part of a lower substrate upper surface in the second embodiment.

A lower substrate 14 is similarly subjected to the hydrophilic treatment. Specifically, the mask plate 88 used in the hydrophilic treatment of the upper substrate 12 is reversed and laid on the lower substrate 14 in which a sensor electrode structure is formed as shown in FIG. 5 (see FIG. 19). And then, the hydrophilic treatment is performed by oxygen plasma exposure in the same manner as in the upper substrate 12. Thereafter, sensor electrodes are coated with certain ion sensitive membranes or oxygen-containing membranes to form sensors, and the upper and lower substrates 12, 14 is laminated to constitute a blood analysis device.

As a hydrophilic treatment method of the surfaces of the substrates 12, 14, in addition to a method in which active oxygen such as an oxygen atom or ozone described herein, may be conducted by surface coatings with hydrophilic inorganic compounds such as titanium oxide ($TiO_2$) and silicon oxide ($SiO_2$) or hydrophilic organic compounds such as poly (2-hydroxyethylmethacrylate) (poly HEMA) and polyvinyl alcohol (PVA).

EXAMPLE 1

A blood analysis device as shown in FIGS. 2, 3, was prepared and attempts were made to perform calibration of an electrochemical sensor, introduction of blood, separation of blood cells and plasma by centrifuge, and analysis of various chemical substance concentrations in plasma. Procedures of the device preparation have been substantially already described. In the blood analysis device used herein, a PET resin was used in a substrate, and a size thereof was a 20 mm square.

As to sensor electrodes, in FIG. 8, the respective sensor electrodes were disposed for analyzing glucose, pH, lactic acid, creatinine, sodium ion, potassium ion, calcium ion, and blood urea nitrogen (BUN) from left side in FIG. 8. As a calibrator solution, Dulbecco's phosphate buffer (PBS, 153.2 mM NaCl, 4.15 mM KCl, pH 7.4) was used with supplement of 1.0 mM $CaCl_2$, 4.0 mM glucose, 5.0 mM urea, 1.0 mM lactic acid, and 100 μM creatinine.

Figure 14:
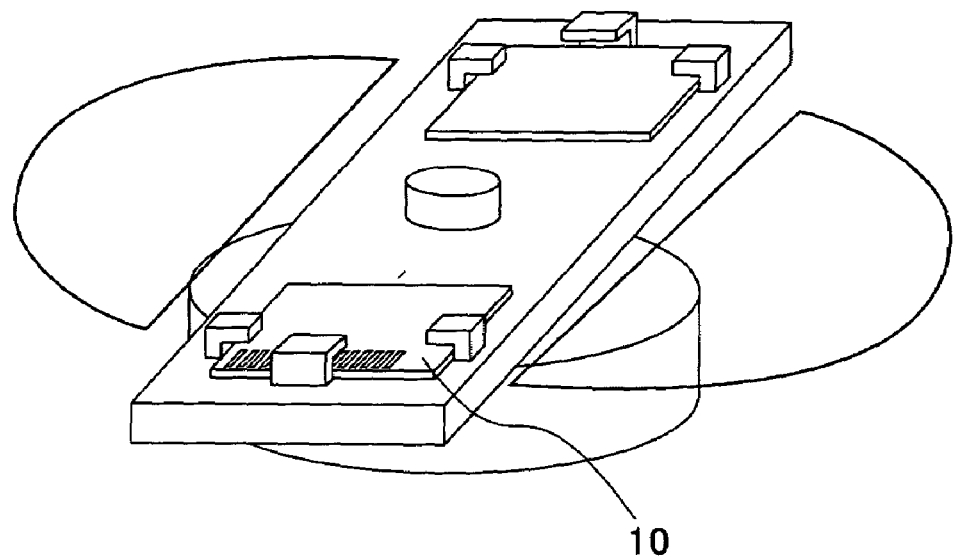
FIG. 14 is an explanatory view of a centrifuging apparatus of the blood analysis device.

After introducing about 1 μL of calibrator solution into a calibrator solution reservoir 16, the analysis device was centrifuged using a centrifugal apparatus shown in FIG. 14 to transfer the calibrator solution to sensor grooves 20 (see FIG. 10). A distance to a rotation radius (from a rotation axis to an outermost portion to which a centrifugal force was most applied on the blood analysis device) was about 25 mm, and the centrifugation was performed at 3,000 rpm for 5 seconds. An analyzed value of the calibrator solution by each sensor was obtained, and each sensor was calibrated. Thereafter, the device was centrifuged at 10,000 rpm for 5 seconds while maintaining a calibrator solution waste reservoir 22 in a second centrifugal force pressurizing direction $F_2$, thereby discharging the calibrator solution from the sensor grooves (see FIG. 11). A painless needle 62 was attached to a blood intake port 40, a healthy male person's forearm vein was stung with the needle, and blood was sucked and introduced from a through hole 36 by a negative-pressure pump (FIG. 12). The blood analysis device was centrifuged again at 10,000 rpm for 60 seconds in such a manner that a plasma separating section (sensor section) 21 was positioned in a first centrifugal force pressurizing direction $F_1$ to convey the blood and separate blood cells and plasma components (FIG. 13). Thereafter, concentrations of eight types of chemical substances, i.e., hydrogen, sodium, potassium, calcium ion, glucose, urea nitrogen, creatinine, and lactic acid in the plasma were analyzed.

Simultaneously, about 10 cc of blood was collected from the same person being tested, and the plasma obtained by the centrifugal separation was analyzed by a conventional method for use in a conventional medical checkup. The pH, sodium ion, potassium ion, and calcium ion were analyzed by an electrode process. Glucose, urea nitrogen (BUN), lactic acid, and creatinine were analyzed using a colorimetric process as a principle. Results of Example 1 and conventional process are shown in Table 1 described later. The analysis result of Example 1 substantially agreed with the result of the conventional process, and a slight difference was in an error range of the sensor on the blood analysis device.

COMPARATIVE EXAMPLE

Figure 15:
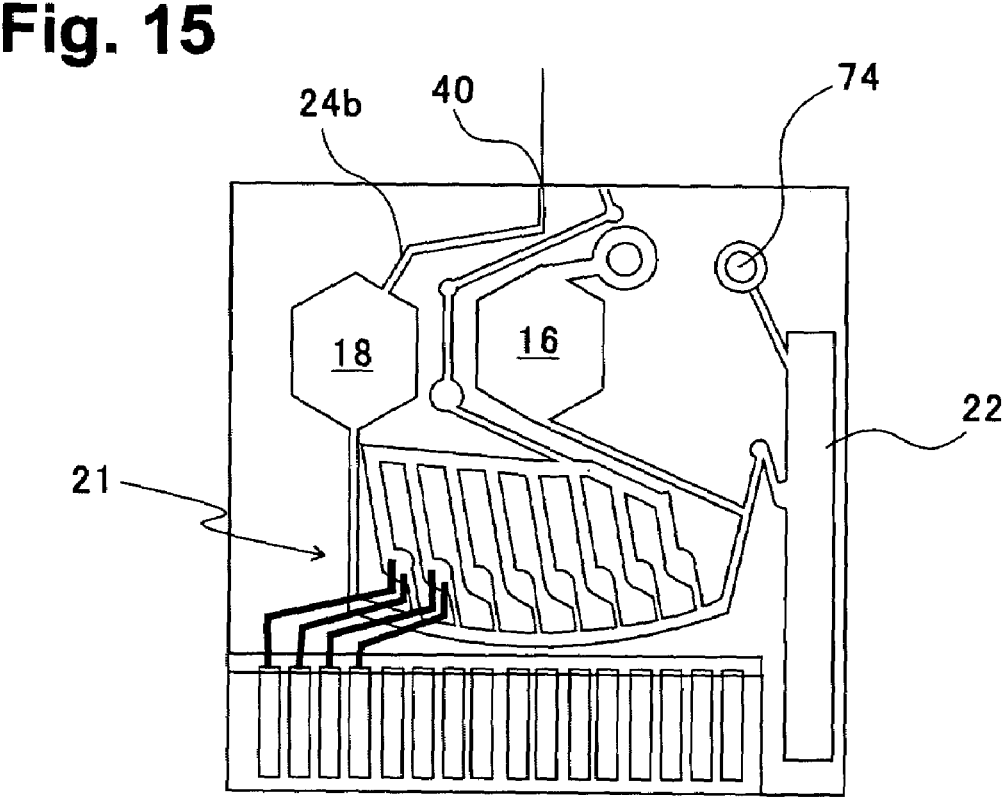
FIG. 15 is an explanatory view showing a structure of the blood analysis device for use in a comparative example of Example 1, in which a pump is used for discharging the calibrator solution.

As a comparative example, a calibrator solution was introduced and discharged using a negative-pressure pump, but not using centrifugation. As shown in FIG. 15, a used blood analysis device was provided with a suction pump connecting port 74 which communicated with a calibrator solution waste reservoir 22, and an air vent passage 32 shown in FIG. 12 was omitted. Another structure is the same as that used in Example 1. Simultaneously with Example 1, the blood of the same person being tested was analyzed using this blood analysis device. An operation is similar to that of the first example other than that a negative-pressure pump connected to the suction pump connecting port 74 was used for the introduction of the calibrator solution into the sensor grooves 20 and discharge of the calibrator solution after calibration.

As analysis results, the results of the conventional process and Example 1 are compared with composition values of used calibrator solutions, and shown in Table 1.

TABLE 1

|  | Conventional Process Analysis | Example 1 (Centrifugal discharge) | Comparative Example (pump discharge) | Calibrator Solution composition |
|---|---|---|---|---|
| pH | 7.4 | 7.4 | 7.3 | 7.4 |
| Na | 140 mM | 140 mM | 146 mM | 153.2 mM |
| K | 3.8 mM | 3.8 mM | 3.9 mM | 4.1 mM |
| Ca | 1.3 mM | 1.2 mM | 1.2 mM | 1.0 mM |
| Glu | 6.1 mM | 6.2 mM | 5.3 mM | 4.0 mM |
| BUN | 4.6 mM | 4.7 mM | 4.7 mM | 5.0 mM |
| Lactic acid | 1.1 mM | 1.1 mM | 1.1 mM | 1.0 mM |
| Creatinine | 86 μM | 89 μM | 92 μM | 100 μM |

In comparison of the analysis result of the comparative example with that of Example 1 in which the calibrator solution was discharged by the centrifugal force, in the comparative example, especially a sodium ion concentration is higher, and a glucose level is lower. This result is supposed to indicate that when the calibrator solution is discharged by the pump, the calibrator solution remains without being completely discharged, and this remaining calibrator solution is mixed with the plasma, and influences the analysis result. The sodium ion concentration of the calibrator solution, and that of the plasma in a case where the calibrator solution is discharged by the centrifugal force are 153.2 mM, 140 mM, respectively. In a case where the calibrator solution is discharged by the pump, the sodium ion concentration in the plasma varies to be close to the concentration in the calibrator solution. In a case where the calibrator solution is discharged by the centrifugal force, glucose concentrations in the calibrator solution and the plasma are 4.0 mM, 6.2 mM. In a case where the calibrator solution is discharged by the pump, glucose concentration in the plasma also fluctuates in a direction brought close to that in the calibrator solution. The concentrations of certain chemical substances in the calibrator solution may be set to be close to values of the concentrations of a healthy person in such a manner that an output result should not fluctuate so much even when the calibrator solution remains. However, as to glucose, creatinine, urea nitrogen, lactic acid and the like, the concentrations fluctuate even with the healthy person depending on conditions such as before/after a meal, morning/evening, a degree of fatigue of a person being tested and the like. Therefore, to analyze these concentrations with a high precision, it is preferable that the calibrator solution is reliably discharged after the sensor calibration. Accordingly, the discharging of the calibrator solution by the centrifugal force is useful for obtaining high-precision analysis results, since the calibrator solution can be discharged reliably as compared with the discharging using the conventional pump or the like.

EXAMPLE 2

Analysis was performed using a plasma fractionated beforehand instead of a whole blood sample. A used blood analysis device is the same as that of the first embodiment. This example is different from Example 1 only in that blood cell/plasma separation is not performed in the analysis device. About 1 cc of vein blood sampled from a person being tested is centrifuged to obtain plasma fraction, and this fraction was introduced into a blood reservoir 18 of a blood analysis device 10 whose sensor was calibrated already. Thereafter, a plasma component was moved to a sensor electrode direction by a centrifugal force. In this case, since the separation of blood cells and plasma from blood is not required, the device was rotated at 500 rpm for 5 seconds to move the plasma. Moreover, concentrations of components in the plasma component were analyzed. Results are shown in Table 2.

TABLE 2

|  | Example 1 (whole blood sample) | Example 2 (plasma sample) | Calibrator composition |
|---|---|---|---|
| pH | 7.4 | 7.2 | 7.4 |
| Na | 140 mM | 141 mM | 153.2 mM |
| K | 3.8 mM | 3.7 mM | 4.1 mM |
| Ca | 1.2 mM | 1.1 mM | 1.0 mM |
| Glu | 6.2 mM | 6.0 mM | 4.0 mM |
| BUN | 4.7 mM | 4.8 mM | 5.0 mM |
| Lactic acid | 1.1 mM | 1.1 mM | 1.0 mM |
| Creatinine | 89 μM | 93 μM | 100 μM |

Results of Example 2 substantially agree with those of Example 1 in which the plasma was separated in the analysis device, but a value of pH is lower than that of Example 1. The value of pH is indicated in terms of a logarithm, and has a large fluctuation. A value of pH 7.2 departs from that of the blood of the healthy person.

EXAMPLE 3

An arrangement of sensor electrodes of a blood analysis device used in Examples 1, 2 was changed from that in Examples 1, 2, and a plasma sample was analyzed. The sensor electrodes were arranged from the left in FIGS. 3, 8 as shown in Table 3. The plasma sample was analyzed in the same manner as in Example 2 using this blood analysis device. Results are shown in Table 4.

TABLE 3

Arrangement of Sensor Electrodes

| Examples 1, 2 | Glu | pH | Lactate | Creatine | Na | K | Ca | BUN |
|---|---|---|---|---|---|---|---|---|
| Example 3 | pH | BUN | Creatine | Na | K | Ca | Lactate | Glu |

TABLE 4

|  | Example 1 (whole blood sample) | Example 2 (plasma sample) | Example 3 (plasma sample) | Conventional Process analysis |
|---|---|---|---|---|
| pH | 7.4 | 7.2 | 7.55 | 7.4 |
| Na | 140 mM | 141 mM | 140 mM | 140 mM |
| K | 3.8 mM | 3.7 mM | 3.8 mM | 3.8 mM |
| Ca | 1.2 mM | 1.1 mM | 1.1 mM | 1.3 mM |
| Glu | 6.2 mM | 6.0 mM | 6.1 mM | 6.1 mM |
| BUN | 4.7 mM | 4.8 mM | 4.8 mM | 4.6 mM |
| Lactic acid | 1.1 mM | 1.1 mM | 1.0 mM | 1.1 mM |
| Creatinine | 89 μM | 93 μM | 93 μM | 86 μM |

Analysis results of Example 3 agree well with those of Example 1 in which the introduced blood was separated into the blood cell and plasma in the blood analysis device, except that a value of pH was high. It is supposed that differential results due to the arrangement of these sensor electrodes are caused by following reasons. In a glucose sensor, hydrogen ions are generated accompanying decomposition of hydrogen peroxide on the electrode as described above. In a lactic acid sensor, pyruvate and hydrogen peroxide are generated from lactic acid and oxygen in the plasma by a function of lactate oxidase enzyme on the electrode, electrons generated at a time when hydrogen peroxide is decomposed are observed as a current amount, and a lactic acid concentration is obtained from the current amount. Simultaneously, hydrogen ions are also generated. Therefore, a hydrogen ion concentration becomes higher in the vicinity of these sensor electrodes, i.e., pH value locally decreases. Accordingly, when the pH sensor electrode is held between the glucose sensor electrode and the lactic acid sensor electrode as in Examples 1, 2, pH sensor electrodes are influenced by a fluctuation of pH in the plasma, and it is supposed that the pH value observed as a result is output as a value lower than an actual value.

On the other hand, in an urea nitrogen (BUN) sensor, ammonia ions and carbon dioxide are generated from urea, hydrogen ions and water in the plasma by the urease reaction, resulting in that the hydrogen ions are consumed. This raises the value of pH. Therefore, it is supposed that the pH sensor outputs a value higher than an actual value in a case where the pH sensor is disposed adjacent to the urea nitrogen sensor electrodes as in Example 3.

On the other hand, in Example 1 (FIG. 13) in which the sensor electrodes are insulated by a blood cell component 72b, such phenomenon is not observed. There were obtained analysis results which were substantially equal to those of a conventional analysis method using a large amount of blood. From this, it has been confirmed that the insulation by the blood cell component performed in Example 1 is very effective in inhibiting mutual interference between the sensor electrodes.

EXAMPLE 4

A calibrator solution reservoir 16, a blood reservoir 18, and introducing channels 34, 36, 24b to these reservoirs described in the second embodiment with reference to FIG. 16 were subjected to a hydrophilic treatment to prepare a blood analysis device, and blood analysis was conducted using the prepared device.

The through hole 36 of an analysis device (substrate) 10 shown in FIG. 16 was spotted with about 1 μL of calibrator solution, and the solution was introduced into the calibrator solution reservoir 16. Since a region of the through hole 36 to the calibrator solution reservoir 16 is subjected to the hydrophilic treatment, the calibrator solution reservoir 16 can be filled quickly by a capillary phenomenon. Thereafter, the calibrator solution was conveyed to sensor grooves 20 using a centrifugal apparatus shown in FIG. 14. After calibration of each sensor, the calibrator solution was discharged from the sensor grooves 20 to a calibrator solution waste reservoir 22 by a centrifugal operation similar to that of Example 1.

A surface of skin of a person being tested is allowed to bleed by several 1L of capillary blood 86 by use of a household capillary blood sampling device 78 shown in FIG. 17, and a blood collecting cylinder 76 attached to the analysis device 10 was brought into contact with this bleeding portion. Blood 86 was instantly drawn into the blood reservoir 18 of the substrate 10 by the capillary phenomenon. When the blood reservoir 18 subjected to the hydrophilic treatment was filled, suction was stopped, and the suction was not observed any more. This indicates that a necessary blood amount is precisely weighed.

After introducing the blood, the blood was transferred to the sensor grooves 20 by the centrifugal operation similar to that of Example 1, and was separated into blood cells and plasma, and concentrations of various chemical substances in the plasma fractionated in each sensor groove were analyzed. Analysis results agreed well with those of Example 1.

INDUSTRIAL APPLICABILITY

As described above, in a blood analysis device of the present invention, a centrifugal operation is possible in two different directions. A sensor section is provided in a plasma separating section and disposed on the side associated with a first centrifugal force pressurizing direction as viewed from a blood introducing channel, a calibrator solution introducing channel, a blood reservoir, and a calibrator solution reservoir, while a calibrator solution waste reservoir is disposed in a second centrifugal force pressurizing direction as viewed from the plasma separating section (sensor section). With such arrangement, the calibrator solution in the calibrator solution reservoir can be conveyed to the sensor section by the centrifugal operation in the first centrifugal direction. After sensor calibration, the calibrator solution can be reliably discharged from the sensor section by centrifuging in the second centrifugal direction. After the calibrator solution discharge, the centrifuging is effected again in the first centrifugal direction, thereby conveying the blood in the blood reservoir to the plasma separating section (sensor section) and effecting separation of blood cells and plasma. Consequently, the analysis can be performed in sensor grooves in the sensor section. Unlike a conventional method, any of blood, plasma and calibrator solution can be conveyed without using any pump. Since the calibrator solution after the calibration can be completely discharged from the sensor grooves by the centrifugal operation, any analysis error is not generated by a remaining calibrator solution.

When the sensor section is provided with a plurality of sensor grooves, the blood introducing channel from the blood reservoir is branched on the side associated with the first centrifugal force pressurizing direction (substrate lower side) to communicate with each of the sensor grooves. A blood cell fraction component in the blood is fractionated in this branched section. The individual sensors can be isolated from each other another by the blood cell fraction. Accordingly, the sensor is not influenced by another adjacent sensor, and higher-precision analysis is possible.

In the case that the blood reservoir and the blood introducing path are subjected to the hydrophilic treatment, a blood sample can be easily introduced into the analysis device by capillary function, and, unlike the conventional method, a negative-pressure pump does not have to be used.

The invention claimed is:

1. A blood analysis device which separates a plasma from a whole blood sample by centrifugation and analyzes a component to be analyzed in blood liquid components, comprising:
   (a) a substrate comprising a sensor for analyzing the component to be analyzed in the blood liquid components;
   (b) a plasma separating section formed in said substrate, and having a sensor groove for housing the sensor, the plasma being separated in the sensor groove when a centrifugal force is applied to the substrate in a first centrifugal direction;
   (c) a blood introducing channel for communicating with said plasma separating section so that a blood sample is introduced into said plasma separating section when the centrifugal force is applied to the substrate in the first centrifugal direction;
   (d) a calibrator solution introducing channel for communicating with said plasma separating section so that a calibrator solution is introduced into said plasma separating section, when the centrifugal force is applied to the substrate in the first centrifugal direction;
   (e) a calibrator solution waste reservoir for communicating with said plasma separating section and allowing the calibrator solution in said plasma separating section to move therein, when the centrifugal force is applied to the substrate in a second centrifugal direction; and
   (f) a calibrator solution discharge channel which allows said plasma separating section to communicate with said calibrator solution waste reservoir, and discharges the calibrator solution in said plasma separating section to said calibrator solution waste reservoir, when the centrifugal force is applied to the substrate in the second centrifugal direction;
   wherein said sensor groove is positioned to discharge the calibrator solution from the sensor groove by action of the centrifugal force in the second centrifugal direction; and
   wherein said calibrator solution waste reservoir is positioned and said calibrator solution discharge channel is disposed so that the calibrator solution contained in the calibrator solution waste reservoir does not flow back into said plasma separating section when the centrifugal force is applied to the substrate in the first centrifugal direction.

2. The blood analysis device according to claim 1, wherein said plasma separating section comprises a plurality of sensor grooves which house a plurality of sensors for analyzing different components to be analyzed, and said blood introducing channel is branched to communicate with each of the plurality of sensor grooves on the side associated with the first centrifugal pressurizing direction of the plasma separating section.

3. The blood analysis device according to claim 2, wherein a portion of the blood introducing channel positioned on the side associated with the first centrifugal force pressurizing direction from said plasma separating section has a capacity to receive a blood cell fraction component in blood in a case where the centrifugal force is applied to the substrate in the first centrifugal direction, and the plasma brought into contact with one of said sensors is isolated from that brought into contact with the other sensor by a blood cell fraction.

4. The blood analysis device according to claim 1, wherein the sensor is an electrochemical sensor.

5. The blood analysis device according to claim 1, wherein a blood collecting needle is attachable to a blood intake port of said blood introducing channel.

6. The blood analysis device according to claim 1, wherein said blood introducing channel is subjected to a hydrophilic treatment.

7. The blood analysis device according to claim 1, wherein said calibrator solution introducing channel is subjected to a hydrophilic treatment.

8. The blood analysis device according to claim 1, further comprising a blood reservoir disposed midway in said blood introducing channel.

9. The blood analysis device according to claim 8, wherein said blood reservoir and the blood introducing channel on an upstream side from the blood reservoir are subjected to a hydrophilic treatment.

10. The blood analysis device according to claim 1, wherein a calibrator solution reservoir is disposed midway in said calibrator solution introducing channel.

11. The blood analysis device according to claim 10, wherein said calibrator solution reservoir, and the calibrator solution introducing channel on an upstream side from the calibrator solution reservoir are subjected to a hydrophilic treatment.

12. The blood analysis device according to claim 1, wherein said first and second centrifugal directions cross each other substantially at right angles.

13. A blood analysis method comprising the steps of:
   (a) providing a blood analysis device comprising a substrate provided with a sensor; a plasma separating section disposed in the substrate, having a sensor groove which houses the sensor, and separating a plasma in the sensor groove; a blood introducing channel which introduces a blood sample into the plasma separating section; a calibrator solution introducing channel which introduces a calibrator solution into the plasma separating section; a calibrator solution waste reservoir; and a calibrator solution discharge channel which connects the plasma separating section to the calibrator solution waste reservoir, and discharges the calibrator solution in the plasma separating section to the calibrator solution waste reservoir;
   (b) supplying the calibrator solution to said calibrator solution introducing channel;

(c) applying a centrifugal force to the substrate in a first centrifugal direction in such a manner that said plasma separating section is disposed in a centrifugal force pressurizing direction, so as to introduce the calibrator solution in the calibrator solution introducing channel into said sensor groove of the plasma separating section;

(d) calibrating said sensor;

(e) rotating said substrate with positioning the substrate in a second centrifugal direction to centrifuge the substrate in such a manner that said calibrator solution reservoir is disposed in the centrifugal force pressurizing direction, and discharging the calibrator solution in the sensor groove to the calibrator solution waste reservoir;

(f) introducing a blood sample into said blood introducing channel;

(g) applying the centrifugal force to the substrate in the first centrifugal direction in such a manner as to dispose the plasma separating section in the centrifugal force pressurizing direction, whereby the blood sample is transferred to the plasma separating section with allowing the plasma separating section to separate blood cells from the plasma, so as to introduce the separated plasma into the sensor groove; and (h) analyzing a liquid component of the plasma in the sensor groove by the sensor.

14. The blood analysis method according to claim 13, wherein said plasma separating section comprises a plurality of sensor grooves, and said blood introducing channel is branched in a first centrifugal direction on the side opposed to each sensor groove to communicate with each sensor groove; and a blood cell fraction in the blood sample is precipitated in a branched portion of said blood introducing channel on the far side associated with the first centrifugal direction by centrifugation in the first direction in said step (g), and the plasma separated as a centrifugal supernatant is positioned in each sensor groove.

15. The blood analysis method according to claim 14, wherein in said steps (g), (h), the plasma introduced into each sensor groove is isolated from the plasma in the other sensor groove by the blood cell fraction which exists in the blood introducing channel branched portion.

16. The blood analysis method according to claim 13, wherein a blood reservoir is provided midway in said blood introducing channel, and the blood reservoir and the blood introducing channel on an upstream side of the blood reservoir are subjected to a hydrophilic treatment; and in said step (f), the blood sample is introduced into the blood reservoir by a capillary function.

17. The blood analysis method according to claim 13, wherein said first and second centrifugal directions cross each other substantially at right angles.

18. The blood analysis device according to claim 2, wherein the sensor is an electrochemical sensor.

19. The blood analysis device according to claim 3, wherein the sensor is an electrochemical sensor.

* * * * *